United States Patent [19]

Cale, Jr. et al.

[11] Patent Number: 5,109,013

[45] Date of Patent: Apr. 28, 1992

[54] 2-(2-SUBSTITUTEDAMINOETHYL)-1,4-DIALKYL-3,4-DIHYDRO-1H-[1,3,5]TRIAZEPINO[3,2-A]BENZIMIDAZOL-5(2H)-ONES AS MUSCLE RELAXANTS

[75] Inventors: Albert D. Cale, Jr., Mechanicsville; Thomas W. Gero, Richmond, both of Va.

[73] Assignee: A. H. Robins Company, Incorporated, Richmond, Va.

[21] Appl. No.: 533,781

[22] Filed: Jun. 6, 1990

[51] Int. Cl.$^5$ .................. A61K 31/915; c07D 487/04
[52] U.S. Cl. .................................... 514/394; 514/395; 540/498
[58] Field of Search ............... 540/498; 514/183, 394, 514/395

[56] References Cited

U.S. PATENT DOCUMENTS 4,352,817 10/1982 Hunkeler et al. .................... 540/498

Primary Examiner—John M. Ford
Assistant Examiner—Jyothsna Venkat
Attorney, Agent, or Firm—Robert F. Boswell

[57] ABSTRACT

Novel compounds of the formula:

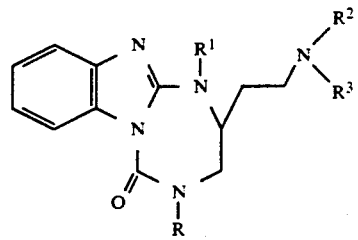

wherein R and $R^1$ are $C_1$-$C_6$ alkyl or cycloalkyl and $R^2$ and $R^3$ are independently selected from $C_1$-$C_6$ alkyl or aryl or —$NR^2R^3$ forms a heterocyclic group which may be further substituted are disclosed. These compounds were found to possess muscle relaxant properties.

15 Claims, No Drawings

2-(2-SUBSTITUTEDAMINOETHYL)-1,4-DIALKYL-3,4-DIHYDRO-1H-[1,3,5]TRIAZEPINO[3,2-A]BENZIMIDAZOL-5(2H)-ONES AS MUSCLE RELAXANTS

BACKGROUND OF THE INVENTION

1. Field of Invention

This invention relates to novel 2-(2-substituted aminoethyl)-1,4-dialkyl 3,4-dihydro-1H-[1,3,5]triazepino[3,2-a]benzimidazol-5(2H)-ones which are useful in treating muscle tension and spasticity in warm blooded animals.

2. Information Disclosure Statement

A search of the chemical and patent literature did not reveal any of the compounds of this invention.

SUMMARY OF THE INVENTION

The [1,3,5]triazepino[3,2-a]benzimidazoles of this invention are of the structure shown by Formula I below:

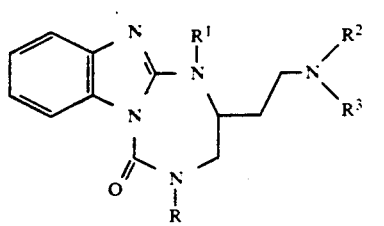

Formula I

Under this formula R and $R^1$ are $C_1$–$C_6$ alkyl or cyclopentyl or cyclohexyl. $R^2$ and $R^3$ are independently selected from $C_1$–$C_6$ alkyl or aryl or $R^2$ and $R^3$ together with the interposing nitrogen form a saturated heterocyclic group such as morpholine, piperidine or piperazine where the piperidine group may be substituted in the 4 position by 4-bis(4-fluorophenyl)methyl or 4-hydroxy and 4-phenyl substituents and the piperazine group may be substituted in the 4-position where the substituent is $C_1$–$C_6$ alkyl, phenyl, 2-pyridinyl, or 2-pyrimidinyl. Also included with Formula I compounds are the optical isomers and pharmaceutically acceptable salts thereof. The $C_1$–$C_6$ alkyl groups include methyl, ethyl, propyl, 2-propyl, butyl, isobutyl, pentyl, hexyl and the like. Aryl is a phenyl group or a phenyl group substituted with from 1 to 3 substituents taken from the group consisting of hydroxy, halogen, $C_1$–$C_4$ alkyloxy, trifluoromethyl, nitro and amino. The term halogen includes fluorine, chlorine, bromine, and iodine.

The term pharmaceutically acceptable salts includes the acid addition salts, solvates, and quaternary salts. The pharmaceutically acceptable acid addition salts includes those formed from strong acids such as hydrochloric acid, hydrobromic acid, sulfuric acid, phosphoric acid, methanesulfonic acid and those formed from weaker acids such as fumaric acid, oxalic acid, cyclohexylsulfamic acid, maleic acid, citric acid and the like.

Solvates include water and/or other solvents utilized in the preparation and purification of Formula I compounds. Quaternary salts include those formed by addition of a $C_1$–$C_6$ alkylhalide such as methyl iodide or ethyl iodide or a benzylic halide such as benzyl bromide.

Muscle relaxant activity is determined using the Straub-tail assay in the mouse as described below.

DETAILED DESCRIPTION OF THE INVENTION

The synthesis of the Formula I compounds of this invention involves the formation of an intermediate 2-(2-chloroethyl)-1,4-dialkyl-3,4-dihydro-1H-[1,3,5]triazepino[3,2-a]benzimidazol-5(2H)-one (2) from N-alkyl-N-(1-alkyl-3-pyrrolidinyl)-1H-benzimidazol-2-amine (1) as shown in the following reaction schemes.

Scheme A

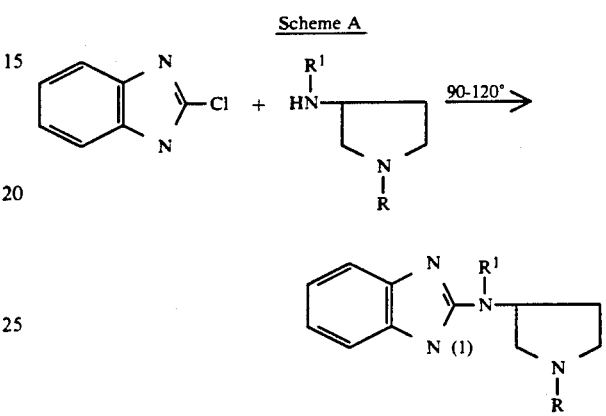

2-chlorobenzimidazole, formed from 2-hydroxybenzimidazole and phosphorus oxychloride, is reacted with an excess of 1-alkyl-3-alkylaminopyrrolidine with or without solvent to form the intermediate (1). A polar solvent such as n-butanol or dimethylformamide can be used.

Scheme B

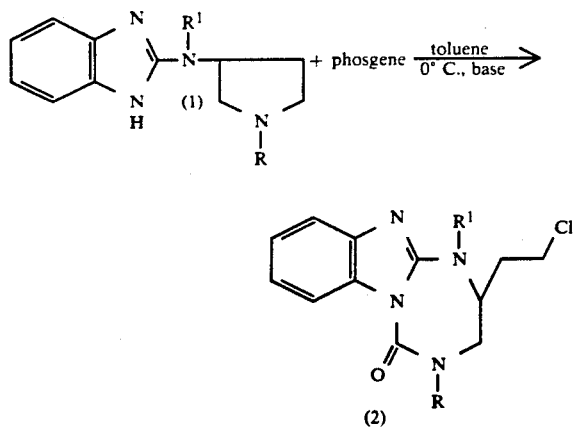

Reaction of the intermediate (1) with phosgene gives the intermediate (2) formed by a ring opening rearrangement reaction. The usual conditions for this reaction are (1) an aprotic solvent such as toluene or methylene chloride, (2) low temperature (0° C.) and (3) addition of a suitable organic base such as diisopropyl ethylamine. This ring-opening/rearrangement reaction was disclosed in our commonly owned U.S. Pat. Nos. 3,337,580 and 3,192,230 and 3,192,221.

Scheme C

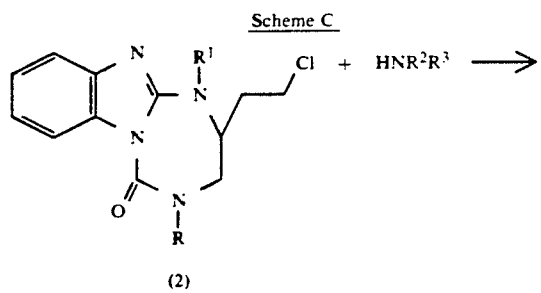

Reacting the intermediate (2) with the appropriate amine (NHR²R³) either with or without solvent yields the Formula I compounds which are isolated by standard extraction and washing techniques and purified by recrystallization, preparative high pressure liquid chromatography (preparative HPLC), or other techniques well known to those skilled in the art.

The 1-alkyl-3-alkylaminopyrrolidines are prepared from 1-alkyl-3-pyrrolidinols as outlined in Scheme D below. The 1-alkyl-3-pyrrolidinols are prepared from a primary alkylamine and 1,4-dibromo-2-butanol by procedures given in J. Med. Pharm. Chem. 1(1), 73–94 (1959) and also J. Med. Chem. 20(10), 1333–1337 (1977).

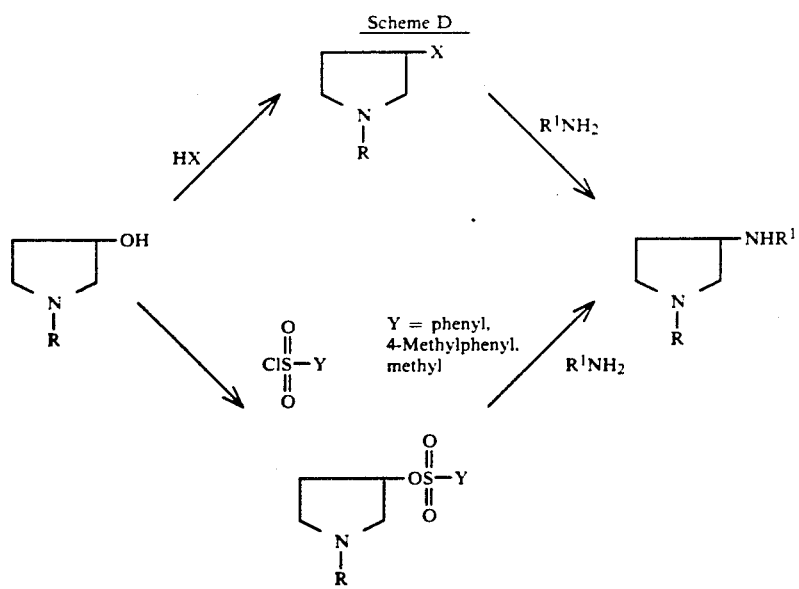

Alternatively the 3-halo or 3-aryl or alkyl sulfonate esters of 1-alkyl pyrrolidinol can be reacted with an N-alkylbenzylamine and the benzyl group of the 1-alkyl-3-(N-benzyl-N-alkyl)aminopyrrolidine subsequently removed by catalytic debenzylation to yield the 1-alkyl-3-alkylaminopyrrolidine. The 3-halopyrrolidines are prepared from the 3-hydroxypyrrolidines by reacting with a hydrogen halide in a suitable solvent and/or by reaction with thionyl chloride. An alternate route to the 1-alkyl-3-bromopyrrolidines is to prepare the 1-alkyl-3-pyrroline from a primary amine and cis-1,4-dichloro-2-butene and hydrobrominate the double bond with HBr.

The foregoing methods of preparation of Formula I compounds and intermediates thereto are broadly described and the reactions may not be applicable as described to each compound included within the scope of this invention. Other synthetic procedures for the preparation of the compounds of Formula I will be apparent to those skilled in the art and this disclosure should not be construed as limiting in any way.

Without further elaboration, it is believed that one skilled in the art will be able to carry out this invention without undue experimentation. The following Preparations and Examples are included for illustrative purposes and should not be construed as limiting to this disclosure in any way. The various reagents used in the following Preparations and Examples are either available commercially or readily synthesized by procedures given in the chemical and patent literature.

PREPARATION 1

N-Methyl-N-(1-methyl-3-pyrrolidinyl)-1H-benzimidazol-2-amine

A mixture of 2-chlorobenzimidazole (25 g, 0.165 mol) and 3-methylamino-1-methylpyrrolidine (72 g, 0.63 mol) was heated at 120° C. with an oil bath for 18 hr. After cooling, 500 ml of 2.5N NaOH solution was added and the mixture extracted twice with 100 ml portions of methylene chloride. The methylene chloride extracts were combined and washed successively with 2×100 ml portions of 2.5N NaOH solution and 3×100 ml portions of water. The methylene chloride solution was dried (Na₂SO₄) and concentrated to obtain 15 g of product (40% yield).

PREPARATION 2

2-(2-Chloroethyl)-3,4-dihydro-1,4-dimethyl-1H-[1,3,5]triazepino[3,2-a]benzimidazol-5(2H)-one To a solution of 35 g of 20% phosgene in toluene (0.071 mol) in 400 mL of $CH_2Cl_2$ cooled to ~0° C. in an ice bath was added a solution of 15 g (0.065 mol) of N-methyl-N-(1-methyl-3-pyrrolidinyl)-1H-benzimidazol-2-amine in 40 mL of $CH_2Cl_2$ dropwise over a period of 1 hr. The ice bath was removed and the reaction mixture allowed to stir at room temperature for 1 hr. The mixture was then cooled to ~0° C. again and a solution of 7.21 g (0.071 mol) of diisopropyl ethylamine in 30 mL of $CH_2Cl_2$ was added dropwise. After the addition was complete, the cooling was removed and the mixture allowed to stir at room temperature for about 45 minutes. The entire reaction mixture was treated with 200 mL of 0.3N NaOH and 3×100 mL of $H_2O$. The organic phase was separated, dried over $Na_2SO_4$, filtered and concentrated by rotary evaporation. Crystallization from isopropyl alcohol afforded 8.0 g of off-white, analytically pure crystals, mp 158°–59° C. Concentration of the mother liquid to half its volume afforded an additional 1.0 g of product, bringing the total yield to 9.0 g (47%).

Analysis: Calculated for $C_{14}H_{12}N_4OCl$: C, 57.44; H, 5.85; N, 19.14;
Found: C, 57.33; H, 5.94; N, 19.13.

PREPARATION 3

2-Chlorobenzimidazole hydrochloride

A mixture of 2-hydroxybenzimidazole (200 g) and phosphorus oxychloride (1100 ml) was heated at reflux temperature for 1 hr and HCl gas was bubbled into the mixture for 3.5 hr. The excess phosphorus oxychloride was removed on a rotary evaporator. The residual oil was poured into ice water (2 L) and a solid impurity was removed by filtration. The filtrate was basified to pH 8 with concentrated ammonium hydroxide. The solid product was collected and dried at 60° C. in vacuo for 18 hrs. The product was recrystallized from acetone to obtain 70 g of the title compound.

PREPARATION 4

1-(1-Methylethyl)-3-pyrroline

Cis-1,4-dichloro-2-butene (25 g, 0.2 mol) was added dropwise to isopropylamine (118 g, 2 mol) with stirring. (Caution: cis-1,4-dichloro-2-butene is a strong irritant and sensitization may occur.) The reaction mixture was then heated at reflux temperature for 2 h. After cooling, ether (200 ml) was added and the mixture filtered. The filter cake was washed with an additional 200 ml of ether. The ether was removed on a rotary evaporator and the residual oil distilled at 110°–122° C. to obtain 10 g (45%) of the title compound.

PREPARATION 5

3-Chloro-1-t-butylpyrrolidine

Hydrogen chloride gas was bubbled into a solution of 1-t-butyl-3-pyrrolidinol (146 g, 1.02 mol) in chloroform (1.01) until the reaction mixture became acidic. A solution of thionyl chloride (1.55 g, 1.3 mol) was added dropwise with warming. After the addition was completed, the reaction mixture was stirred at reflux temperature for 18 h. The chloroform and excess thionyl chloride was removed on a rotary evaporator. Cracked ice and water was added to the residue and the mixture basified with 25% sodium hydroxide solution. The mixture was extracted with chloroform, and the extract washed with brine solution. The extract was dried ($Na_2SO_4$), concentrated and distilled at 75° C./15 mm to obtain 104 g (63%) of the title compound.

PREPARATION 6

3-Bromo-1-ethylpyrrolidine

1-Ethyl-3-pyrroline (19.2 g, 0.193 mol) was added dropwise to 48% aqueous hydrobromic acid solution (60 ml). Hydrogen bromide gas was bubbled into the reaction mixture while the mixture was heated at reflux temperature for 16 h. After cooling, the reaction mixture was poured onto crushed ice and the mixture basified with 50% aqueous sodium hydroxide solution. The mixture was extracted with diisopropyl ether. The extract was dried ($MgSO_4$), concentrated, and the residual oil distilled at 120°–125° C. (150 mm) to obtain 24.5 g (71.5%) of the title compound.

PREPARATION 7

1-Cyclohexyl-3-pyrrolidinol

With stirring 1,4-dibromo-2-butanol (696 g, 3 mol) was added dropwise to cyclohexylamine (595 g, 6 mol). The addition was rapid until the reaction temperature reached 130° C. and then slowed so as to maintain the temperature at 130°–135° C. When the addition was completed the mixture was heated at 130° C. for 2 h. The mixture was then poured into 3 L of water with stirring. The aqueous mixture was filtered and the filtrate extracted with 1 L of ether. The aqueous solution was basified with 50% sodium hydroxide solution. The oil which separated from solution was removed. The aqueous layer was extracted with three 400 ml portions of ether and the extract combined with the oil. The ether solution was dried ($Na_2SO_4$) and concentrated. The residual oil was distilled and the fraction boiling at 165°–180° C./39 mm was collected. A higher boiling fraction (180°–190° C./39 mm) was collected and redistilled to give some additional material boiling at 165°–180° C./39 mm for a total yield of 329.6 g (77%).

PREPARATION 8

1-Cyclohexyl-3-methylaminopyrrolidine

A mixture of 40% aqueous methylamine (93 g), ethanol (200 ml) and 3-bromo-1-cyclohexylpyrrolidine (92.8 g, 0.4 mol) was heated to 150° C. in a steel bomb for 20 hr. After cooling, the mixture was concentrated and the residue partitioned between dilute sodium hydroxide and chloroform. The chloroform solution was dried (sodium sulfate), concentrated, and the residue distilled to obtain 40 g (55%), bp 172°–176° C./40 mm. A portion of the distillate was converted to the fumarate salt which was recrystallized from ethanol-water. This was converted back to the free base and distilled, bp 75°–80° C./0.1 mm.

Analysis: Calculated for $C_{11}H_{22}N_2$: C, 72.47; H, 12.16; N, 15.37;
Found: C, 72.24; H, 12.26; N, 15.26.

PREPARATION 9

1-t-Butyl-3-pyrrolidinol

With stirring, t-butylamine (146.2 g, 2.0 mol) was heated to reflux. The heat was removed and 1,4-dichloro-2-butanol added dropwise at such a rate that a gentle reflux was maintained. When the addition was completed the mixture was stirred for 10 min without heat and then heat reapplied. The reaction mixture began to reflux at 64° C. and over a period of 4 h the pot temperature rose to 130°-135° C. The temperature was held at 130°-135° C. for 1 h. Cold water (500 ml) was added and the mixture acidified with concentrated hydrochloric acid. The mixture was washed with ether and basified strongly with 50% sodium hydroxide solution, forming 2 layers. The lower aqueous layer was extracted with ether and the extract combined with the oily upper layer. The solution was dried (sodium sulfate) and the ether and excess t-butylamine removed on a rotary evaporator. The residual oil was distilled to obtain 81 g (57%) of the title compound, bp 145°-147° C./~30 mm.

PREPARATION 10

1-t-Butyl-3-(t-butylamino)pyrrolidine

A solution of 1-t-butyl-3-pyrrolidinol (81 g, 0.565 mol) in 50 ml of dry toluene was added dropwise to a stirred slurry of sodium amide (22 g, 0.565 mol) in 150 ml of dry toluene at 28°-33° C. After the addition was completed the reaction temperature was increased to 40° C. After 3 h. at 40° C. ammonia formed in the reaction was removed via water aspirator vacuum. The reaction mixture was chilled to 5°-8° C. and a solution of p-toluenesulfonyl chloride (107.5 g, 0.565 mol) in 250 ml dry toluene was added dropwise. The mixture was stirred overnight at ambient temperature. The reaction mixture was then washed with two 250 ml portions of water and the toluene layer dried (sodium sulfate) and then concentrated to yield 155 g (93%) of the intermediate 1-t-butyl-3-pyrrolidinol tosylate ester (oil).

The tosylate ester and t-butylamine (125 g, 1.71 mol) were sealed in a steel bomb and heated on a steam bath for 15.5 h. The bomb was cooled and the contents partitioned between ether and water. The ether layer was washed with water, dried over sodium sulfate, and concentrated to an oil. The residual oil was distilled to obtain 28.8 g (35.6%) of the title compound, bp 135°-143° C./~30 mm.

PREPARATION 11

1-methyl-3-pyrrolidine methanesulfonate ester

Methanesulfonyl chloride (68.4 g, 0.6 mol) was added slowly dropwise to a rapidly stirred solution of 1-methyl-3-pyrrolidinol (50.5 g, 0.50 mol) and triethylamine (60.6 g, 0.6 mol) in 500 ml of dry benzene under a nitrogen atmosphere. The reaction was exothermic and was cooled by a cold water bath. When the addition was completed the mixture was stirred at ambient temperature overnight. Isopropyl ether (250 ml) was added to precipitate the triethylamine hydrochloride which was removed by filtration. The filtrate was concentrated to a brown oil. The oil was dissolved in methylene chloride (300 ml) and concentrated again to remove any remaining triethylamine or methanesulfonyl chloride. The yield was 90.1 g.

PREPARATION 12

3-butylamino-1-methylpyrrolidine

A mixture of 1-methyl-3-pyrrolidinol methanesulfonate ester (90 g, 0.5 mol) and n-butylamine (230 g, 3 mol) was heated at reflux temperature under a nitrogen atmosphere for 3 hr and at ambient temperature for 72 hr. The reaction was concentrated on a rotary evaporator to a dark oil. The oil was partitioned between 3N hydrochloric acid solution and benzene. The acid layer was basified with 50% sodium hydroxide solution and extracted with benzene. The extract was dried (magnesium sulfate) and concentrated to obtain 65 g of light colored oil. The oil was distilled, first under aspirator vacuum and then under high vacuum (0.25 mm). A pure fraction of the title compound distilled at 100°-105° C. (15 mm). A small sample was converted to the dioxalate salt, mp 188°-190° C.

Analysis: Calculated for $C_{13}H_{24}N_2O_8$: C, 46.42; H, 7.19; N, 8.33;

Found: C, 46.05; H, 7.04; N, 8.13.

PREPARATION 13

Following the procedure of Preparation 5 and substituting for 1-t-butyl-3-pyrrolidinol the following:
a. 1-hexyl-3-pyrrolidinol
b. 1-cyclopentyl-3-pyrrolidinol
there are obtained respectively:
a. 3-chloro-1-hexylpyrrolidine
b. 3-chloro-1-cyclopentylpyrrolidine

PREPARATION 14

Following the procedure of Preparation 8 and substituting for 3-bromo-1-cyclohexylpyrrolidine:
a. 3-chloro-1-hexylpyrrolidine
b. 3-chloro-1-cyclopentylpyrrolidine
there are obtained respectively:
a. 1-hexyl-3-methylaminopyrrolidine
b. 1-cyclopentyl-3-methylaminopyrrolidine.

PREPARATION 15

Following the procedure of Preparation 8 and substituting for methylamine and 3-bromo-1-cyclohexylpyrrolidinol the following:
a. ethylamine and 3-chloro-1-methylpyrrolidine
b. n-propylamine and 3-chloro-1-methylpyrrolidine
c. methylamine and 3-chloro-1-(1-methylethyl)pyrrolidine
d. n-butylamine and 3-chloro-1-isobutylpyrrolidine
e. cyclohexylamine and 3-chloro-1-methylpyrrolidine,
f. ethylamine and 3-chloro-1-ethylpyrrolidine
there are obtained respectively:
a. 3-ethylamino-1-methylpyrrolidine
b. 1-methyl-3-(propylamino)pyrrolidine
c. 3-methylamino-1-(1-methylethyl)pyrrolidine
d. 3-butylamino-1-(2-methylpropyl)pyrrolidine
e. 3-cyclohexylamino-1-methylpyrrolidine
f. 1-ethyl-3-ethylaminopyrrolidine.

PREPARATION 16

Following the procedures of Preparation 10 and substituting for t-butylamine and 1-t-butyl-3-pyrrolidinol the following:
a. Ethylamine and 1-butyl-3-pyrrolidinol
b. methylamine and 1-(1-methylethyl)-3-pyrrolidinol
c. butylamine and 1-cyclohexyl-3-pyrrolidinol
there are obtained respectively:
a. 1-butyl-3-ethylaminopyrrolidine
b. 1-(1-methylethyl)-3-methylaminopyrrolidine
c. 3-butylamino-1-cyclohexylpyrrolidine.

PREPARATION 17

Following the procedure of Preparation 1 and substituting for 3-methylamino-1-methylpyrrolidine:
a. 1-cyclohexyl-3-methylaminopyrrolidine b. 1-t-butyl-3-(t-butylamino)pyrrolidine
c. 3-ethylamino-1-methylpyrrolidine
d. 1-methyl-3-(propylamino)pyrrolidine
e. 3-methylamino-1-(1-methylethyl)pyrrolidine
f. 3-butylamino-1-(2-methylpropyl)pyrrolidine
g. 3-cyclohexylamino-1-methylpyrrolidine
h. 1-ethyl-3-(ethylamino)pyrrolidine
i. 1-butyl-3-ethylaminopyrrolidine
j. 3-(methylamino)-1-(1-methylethyl)pyrrolidine
k. 3-butylamino-1-cyclohexylpyrrolidine
l. 3-butylamino-1-methylpyrrolidine
m. 1-hexyl-3-methylaminopyrrolide
n. 1-cyclopentyl-3-methylaminopyrrolidine there are obtained respectively:
a. N-methyl-N-(1-cyclohexyl-3-pyrrolidinyl)-1H-benzimidazol-2-amine
b. N-(t-butyl)-N-(1-t-butyl-3-pyrrolidinyl)-1H-benzimidazol-2-amine
c. N-ethyl-N-(1-methyl-3-pyrrolidinyl)-1H-benzimidazol-2-amine
d. N-propyl-N-(1-methyl-3-pyrrolidinyl)-1H-benzimidazol-2-amine
e. N-methyl-N-[1-(1-methylethyl)-3-pyrrolidinyl]-1H-benzimidazol-2-amine
f. N-butyl-N-[1-(2-methylpropyl)-3-pyrrolidinyl]-1H-benzimidazol-2-amine
g. N-cyclohexyl-N-(1-methyl-3-pyrrolidinyl)-1H-benzimidazol-2-amine
h. N-ethyl-N-(1-ethyl-3-pyrrolidinyl)-1H-benzimidazol-2-amine
i. N-ethyl-N-(1-butyl-3-pyrrolidinyl)-1H-benzimidazol-2-amine
j. N-methyl-N-[1-(1-methylethyl)-3-pyrrolidinyl]-1H-benzimidazol-2-amine
k. N-butyl-N-(1-cyclohexyl-3-pyrrolidinyl)-1H-benzimidazol-2-amine
l. N-butyl-N-(1-methyl-3-pyrrolidinyl)-1H-benzimidazol-2-amine
m. N-methyl-N-(1-hexyl-3-pyrrolidinyl)-1H-benzimidazol-2-amine
n. N-methyl-N-(1-cyclopentyl-3-pyrrolidinyl)-1H-benzimidazol-2-amine.

PREPARATION 18

Following the procedures of Preparation 2 and substituting the following for N-methyl-N-(1-methyl-3-pyrrolidinyl)-1H-benzimidazol-2-amine:
a. N-methyl-N-(1-cyclohexyl-3-pyrrolidinyl)-1H-benzimidazol-2-amine
b. N-(t-butyl)-N-(1-t-butyl-3-pyrrolidinyl)-1H-benzimidazol-2-amine
c. N-ethyl-N-(1-methyl-3-pyrrolidinyl)-1H-benzimidazol-2-amine
d. N-propyl-N-(1-methyl-3-pyrrolidinyl)-1H-benzimidazol-2-amine
e. N-methyl-N-[1-(1-methylethyl)-3-pyrrolidinyl]-1H-benzimidazol-2-amine
f. N-butyl-N-[1-(2-methylpropyl)-3-pyrrolidinyl]-1H-benzimidazol-2-amine
g. N-cyclohexyl-N-(1-methyl-3-pyrrolidinyl)-1H-benzimidazol-2-amine
h. N-ethyl-N-(1-ethyl-3-pyrrolidinyl)-1H-benzimidazol-2-amine
i. N-ethyl-N-(1-butyl-3-pyrrolidinyl)-1H-benzimidazol-2-amine
j. N-methyl-N-[1-(1-methylethyl)-3-pyrrolidinyl]-1H-benzimidazol-2-amine
k. N-butyl-N-(1-cyclohexyl-3-pyrrolidinyl)-1H-benzimidazol-2-amine
l. N-butyl-N-(1-methyl-3-pyrrolidinyl)-1H-benzimidazol-2-amine
m. N-methyl-N-(1-hexyl-3-pyrrolidinyl)-1H-benzimidazol-2-amine
n. N-methyl-N-(1-cyclopentyl-3-pyrrolidinyl)-1H-benzimidazol-2-amine there are obtained respectively:
a. 2-(2-chloroethyl)-3,4-dihydro-1-methyl-4-cyclohexyl-1H-[1,3,5]triazepino[3,2-a]benzimidazol-5(2H)-one
b. 2-(2-chloroethyl)-3,4-dihydro-1,4-di-t-butyl-1H-[1,3,5]triazepino[3,2-a]benzimidazol-5(2H)-one
c. 2-(2-chloroethyl)-3,4-dihydro-1-ethyl-4-methyl-1H-[1,3,5]triazepino[3,2-a]benzimidazol-5(2H)-one
d. 2-(2-chloroethyl)-3,4-dihydro-4-methyl-1-propyl-1H-[1,3,5]triazepino[3,2-a]benzimidazol-5(2H)-one
e. 2-(2-chloroethyl)-3,4-dihydro-1-methyl-4-(1-methylethyl)-[1,3,5]triazepino[3,2-a]benzimidazol-5(2H)-one
f. 1-butyl-2-(2-chloroethyl)-3,4-dihydro-4-(2-methylpropyl)-[1,3,5]triazepino[3,2-a]benzimidazol-5(2H)-one
g. 2-(2-chloroethyl)-1-cyclohexyl-3,4-dihydro-4-methyl-1H-[1,3,5]triazepino[3,2-a]benzimidazol-5(2H)-one
h. 2-(2-chloroethyl)-1,4-diethyl-3,4-dihydro-1H-[1,3,5]triazepino[3,2-a]benzimidazol-5(2H)-one
i. 4-butyl-2-(2-chloroethyl)-3,4-dihydro-1-ethyl-1H-[1,3,5]triazepino-[3,2-a]benzimidazol-5(2H)-one
j. 2-(2-chloroethyl)-3,4-dihydro-1-methyl-4-(1-methylethyl)-[1,3,5]triazepino[3,2-a]benzimidazol-5(2H)-one
k. 1-butyl-2-(2-chloroethyl)-4-cyclohexyl-3,4-dihydro-1H-[1,3,5]triazepino[3,2-a]benzimidazol-5(2H)-one
l. 1-butyl-2-(2-chloroethyl)-3,4-dihydro-4-methyl-1H-[1,3,5]triazepino[3,2-a]benzimidazol-5(2H)-one
m. 2-(2-chloroethyl)-3,4-dihydro-4-hexyl-1-methyl-1H-[1,3,5]triazepino[3,2-a]benzimidazol-5(2H)-one
n. 2-(2-chloroethyl)-4-cyclopentyl-3,4-dihydro-1-methyl-1H-[1,3,5]triazepino[3,2-a]benzimidazol-5(2H)-one.

EXAMPLE 1

3,4-Dihydro-1,4-dimethyl-2[2-(4-morpholinyl)ethyl]-1H-[1,3,5]triazepino[3,2-a]benzimidazol-5(2H)-one To 3.0 g (0.0103 mol) of 2-(2-chloroethyl)-3,4-dihydro-1,4-dimethyl-1H-[1,3,5]triazepino[3,2-a]benzimidazol-5(2H)-one was added 20 mL of morpholine. The mixture was stirred at 60° C. for 4 hr. The morpholine was removed at 60° C. and approximately 1 mm Hg. The residue was partitioned between 100 mL of CH$_2$Cl$_2$ and 100 mL of 1N NaOH. The basic layer was reextracted with 50 mL of CH$_2$Cl$_2$. The combined organic extracts were dried over Na$_2$SO$_4$, filtered, and concentrated by rotary evaporation. The residue was crystallized from isopropyl alcohol to afford 2.1 g (59%) of white analytically pure crystals, mp 149°-151.5° C.

Analysis: Calculated for C$_{18}$H$_{25}$N$_5$O$_2$: C, 62.95; H, 7.34; N, 20.39;
Found: C, 62.82; H, 7.40; N, 20.33.

EXAMPLE 2

2-[2-(Dimethylamino)ethyl]-3,4-dihydro-1,4-dimethyl-1H-[1,3,5]triazepino[3,2-a]benzimidazol-5(2H)-one monohydrate To 90 mL of freshly collected dimethylamine and 10 mL of methanol was added 3.25 g (0.011 mol) of 2-(2-chloroethyl)-3,4-dihydro-1,4-dimethyl-1H-

[1,3,5]triazepino[3,2-a]benzimidazol-5(2H)-one. The reaction flask was sealed and left standing at room temperature for 6 days. The dimethylamine was then allowed to evaporate at room temperature and the residue partitioned between 75 mL of 1N NaOH and 75 mL of $CH_2Cl_2$. The organic phase was washed with another 50 mL of 1N NaOH. The combined organic layers were dried over $Na_2SO_4$, filtered, and concentrated by rotary evaporation. The solid residue was recrystallized from isopropyl ether to give 2.8 g of white analytically pure crystals, mp 91°–95° C.

Analysis: Calculated for $C_{16}H_{25}N_5O_2$: C, 60.17; H, 7.89; N, 21.93;

Found: C, 60.28; H, 7.01; N, 21.86.

EXAMPLE 3

3,4-Dihydro-1,4-dimethyl-2-[2-(4-methyl-1-piperazinyl)ethyl]-1H-[1,3,5]triazepino[3,2-a]benzimidazol-5(2H)-one (E)-2-butenedioate (1:2)

To 20 mL of N-methylpiperazine was added 3.0 g (0.01 mol) of 2-(2-chloroethyl)-3,4-dihydro-1,4-dimethyl-1H-[1,3,5]triazepino[3,2-a]benzimidazol-5(2H)-one. The reaction mixture was heated to 60° C. for 24 hr. The excess amine was removed at 70° C., 0.5 mm Hg. The residual oil was taken up in 60 mL of $CH_2Cl_2$ and washed with 2×50 mL of 1N NaOH. The organic layer was dried over $Na_2SO_4$, filtered, concentrated by rotary evaporation, and further concentrated at 90° C., 0.5 mm Hg. The residual oil/glass was treated with 2 equivalent of fumaric acid isopropyl alcohol to give 3.4 g of solid. This was recrystallized from isopropyl alcohol to give 3.0 g (51%) off-white analytically pure material, mp 171°–79° C.

Analysis: Calculated for $C_{22}H_{36}N_6O_9$: C, 55.10; H, 6.17; N, 14.58;

Found: C, 55.00; H, 6.45; N, 14.32.

EXAMPLE 4

3,4-Dihydro-1,4-dimethyl-2-[2-(methylphenylamino)ethyl]-1H-[1,3,5]triazepino[3,2-a]benzimidazol-5(2H)-one To 15 mL of N-methylaniline was added 3.0 g (0.01 mol) of 2-(2-chloroethyl)-3,4-dihydro-1,4-dimethyl-1H-[1,3,5]triazepino[3,2-a]benzimidazol-5(2H)-one. The reaction was heated at 60° C. for 1.5 hr, then 100° C. for ~48 hr. The N-methylaniline was removed by distillation. The residue was dissolved in 100 mL of $CH_2Cl_2$, washed with 2×100 mL of 1N NaOH and dried over $Na_2SO_4$. The organic phase was filtered and concentrated by rotary evaporation. The residue was then heated to 100° C., 0.5 mm Hg to remove any residual starting amine. The crude syrup was crystallized from toluene/iso-octane to afford 2.0 g (55%) of white analytically pure crystals, mp 74°–90° C.

Analysis: Calculated for $C_{21}H_{25}N_5$: C, 69.40; H, 6.93; N, 19.27;

Found: C, 69.25; H, 7.16; N, 18.93.

EXAMPLE 5

2-[2-[4-[Bis(4-fluorophenyl)methyl]-1-piperidinyl]ethyl]-3,4-dihydro-1,4-dimethyl-1H-[1,3,5]-triazepino[3,2-a]benzimidazol-5(2H)-one To a solution of 50 mL of toluene containing 4.0 g (0.04 mol) of triethylamine was added 3.0 g (0.01 mol) of 2-(2-chloroethyl)-3,4-dihydro-1,4-dimethyl-1H-[1,3,5]triazepino[3,2-a]benzimidazol-5(2H)-one and 4.0 g (0.014 mol) of 4-[bis(4-fluorophenyl)methyl]piperidine. The mixture was heated to reflux for 3 days after which time 1.0 g (0.003 mL) of 4-[bis(4-fluorophenyl)methyl]piperidine and 1.0 g (0.01 mol) of triethylamine was added. Heating under reflux was continued for 24 hr. The solvent was removed by rotary evaporation and the residue dissolved in 100 mL of $CH_2Cl_2$. The organic phase was washed with 2×100 mL of 1N NaOH, dried over $Na_2SO_4$, filtered, and concentrated by rotary evaporation. The residue was subjected to preparative HPLC using silica gel as the stationary phase and eluting with ethanol. Combination of like fractions afforded 3.1 g (57%) of analytically pure material as a glass.

Analysis: Calculated for $C_{32}H_{35}N_5OF_2$: C, 70.70; H, 6.49; N, 12.88;

Found: C, 70.44; H, 6.50; N, 12.84.

EXAMPLE 6

3,4-Dihydro-1,4-dimethyl-2-[2-(4-phenyl-1-piperazinyl)ethyl]-1H-[1,3,5]triazepino[3,2-a]benzimidazol-5(2H)-one hemihydrate To a 50 mL of toluene containing 3.0 g (0.03 mol) of triethylamine and 2.94 g (0.0183 mol) of N-phenylpiperazine was added 3.5 g (0.012 mol) of 2-(2-chloroethyl)-3,4-dihydro-1,4-dimethyl-1H-[1,3,5]triazepino[3,2-a]benzimidazol-5(2H)-one. The reaction mixture was heated to reflux for 7 days. (Note: 3.19 g (0.02 mol) of N-phenylpiperazine was added after ~2 days followed by 1.60 g (0.1 mol) after ~2 additional days during the week). After cooling to room temperature, the entire reaction mixture was treated with ~5 mL of acetic anhydride and stirred at room temperature for 2 hr. The reaction mixture was washed with 2×50 mL of 1N NaOH, dried over $Na_2SO_4$, filtered and concentrated by rotary evaporation. The residue was subjected to preparative HPLC using isopropyl alcohol as the eluent and silica gel as the stationary phase. Like fractions were combined and concentrated by rotary evaporation to give 2.7 g (53%) of a glass.

Analysis: Calc. for $C_{24}H_{30}N_6O \cdot 0.5H_2O$: C, 67.42; H, 7.31; N, 19.66;

Found: C, 67.89; H, 7.16; N, 19.65.

EXAMPLE 7

3,4-Dihydro-2-[2-(4-hydroxy-4-phenyl-1-piperidinyl)ethyl]-1,4-dimethyl-1H-[1,3,5]-triazepino[3,2-a]benzimidazol-5(2H)-one (Z)-2-butenedioate (1:1), hemihydrate To a solution of 3.0 g (0.03 mol) of triethylamine in 60 mL of toluene was added 3.5 g (0.012 mol) of 2-(2-chloroethyl)-3,4-dihydro-1,4-dimethyl-1H-[1,3,5]triazepino[3,2-a]benzimidazol-5(2H)-one and 3.5 g (0.020 mol) of 4-hydroxy-4-phenylpiperidine. The reaction mixture was heated to reflux for 24 hr and 1.35 g (0.0076 mol) of 4-hydroxy-4-phenylpiperidine was added. After another 24 hr an additional 1.00 g (0.0056 mol) of 4-hydroxy-4-phenylpiperidine was added. After another 24 hr, the reaction mixture was filtered and the solvent removed by rotary evaporation. The residue was dissolved in $CH_2Cl_2$ (~100 mL), washed with ~50 mL of 1N NaOH. The organic layer was dried over $Na_2SO_4$, filtered, concentrated by rotary evaporation, and subjected to preparative HPLC using 8% triethylamine in ethyl acetate as the eluent and silica gel as the stationary phase. Similar fractions were combined and the dimaleate salt was made in two separate batches and recrystallized together to give 2.4 g (30%) of analytically pure white crystals, mp 135°–39° C.

Analysis: Calc. for $C_{33}H_{39}N_5O_{10}.0.5H_2O$: C, 58.75; H, 5.98; N, 10.38;
Found: C, 58.32; H, 5.98; N, 10.02.

EXAMPLE 8

3,4-Dihydro-1,4-dimethyl-2-[2-[4-(2-pyridinyl)-1-piperazinyl]ethyl]-1H-[1,3,5]-triazepino[3,2-a]benzimidazol-5(2H)-one hemihydrate To 50 mL of toluene was added 5.0 g (0.0171 mol) of 2-(2-chloroethyl)-3,4-dihydro-1,4-dimethyl-1H-[1,3,5]triazepino[3,2-a]benzimidazol-5(2H)-one, 5.58 g (0.034 mol) of 2-(2-pyridyl)piperazine, and 3.4 g (0.034 mol) of triethylamine, and the entire reaction mixture heated to reflux. After 2 days, 1.5 g (0.009 mol) of 1-(2-pyridinyl)piperazine was added and reflux continued for 24 hours. The reaction mixture was washed with 2×50 mL of 1N NaOH, dried over $Na_2SO_4$, filtered and concentrated by rotary evaporation. The residue was subjected to preparative HPLC using silica gel as the stationary phase and eluting with 5% triethylamine in acetone. Like fraction were combined affording ~4.0 g (55%) of a glass.

Analysis: Calc. for $C_{23}H_{29}N_7O.5H_2O$: C, 64.46; H, 7.06; N, 22.88;
Found: C, 64.90; H, 6.94; N, 22.53.

EXAMPLE 9

3,4-Dihydro-1,4-dimethyl-2-[2-[4-(2-pyrimidinyl)-1-piperazinyl]ethyl]-1H-[1,3,5]-triazepino[3,2-a]benzimidazol-5(2H)-one (E)-2-butenedioate (2:3)

A solution of 4.0 g (0.0137 mol) of 2-(2-chloroethyl)-3,4-dihydro-1,4-dimethyl-1H-[1,3,5]triazepino[3,2-a]benzimidazol-5(2H)-one, 7.0 g (0.043 mol) of 1-(2-pyrimidinyl)-piperazine, and 4.0 g (0.04 mol) of triethylamine in ~50 mL of toluene was heated to reflux for 48 hr. The reaction mixture was washed with 2×50 mL of 1N NaOH, dried over $Na_2SO_4$, filtered, and concentrated by rotary evaporation. The residue was subjected to preparative HPLC using acetone as the eluent and silica gel as the stationary phase. Like fractions were combined and treated with fumaric acid in isopropyl alcohol. The crude crystals were recrystallized from isopropyl alcohol to give ~4.5 g (55%) of analytically pure, white crystals, mp 208° C. (dec).

Analysis: Calculated for $C_{28}H_{34}N_8O_7$: C, 56.56; H, 5.77; N, 18.84;
Found: C, 56.52; H, 5.97; N, 18.44.

EXAMPLE 10

Following the procedures of Example 1 there are obtained from:
a. 2-(2-chloroethyl)-3,4-dihydro-1,4-dicyclohexyl-1H-[1,3,5]triazepino[3,2-a]benzimidazol-5(2H)-one
b. 2-(2-chloroethyl)-3,4-dihydro-1,4-di-t-butyl-1H-[1,3,5]triazepino[3,2-a]benzimidazol-5(2H)-one
c. 2-(2-chloroethyl)-3,4-dihydro-1-ethyl-4-methyl-1H-[1,3,5]triazepino[3,2-a]benzimidazol-5(2H)-one
the following compounds respectively:
a. 3,4-dihydro-1,4-dicyclohexyl-2-[2-(4-morpholinyl)ethyl]-1H-[1,3,5]triazepino[3,2-a]benzimidazol-5(2H)-one
b. 3,4-dihydro-1,4-di-t-butyl-2-[2-(4-morpholinyl)ethyl]-1H-[1,3,5]triazepino[3,2-a]benzimidazol-5(2H)-one
c. 3,4-dihydro-1-ethyl-4-methyl-2-[2-(4-morpholinyl)ethyl]-1H-[1,3,5]triazepino[3,2-a]benzimidazol-5(2H)-one.

EXAMPLE 11

Following the procedures of Example 2, there are obtained from dimethylamine and
a. 2-(2-chloroethyl)-3,4-dihydro-4-methyl-1-propyl-1H-[1,3,5]triazepino[3,2-a]benzimidazol-5(2H)-one
b. 2-(2-chloroethyl)-3,4-dihydro-1-methyl-4-(1-methylethyl)-1H-[1,3,5]-triazepino[3,2-a]benzimidazol-5(2H)-one
c. 1-butyl-2-(2-chloroethyl)-3,4-dihydro-4-(2-methylpropyl)-1H-[1,3,5]-triazepino[3,2-a]benzimidazol-5(2H)-one
the following compounds respectively:
a. 3,4-dihydro-2-[2-(dimethylamino)ethyl]-4-methyl-1-propyl-1H-[1,3,5]triazepino[3,2-a]benzimidazol-5(2H)-one
b. 3,4-dihydro-2-[2-(dimethylamino)ethyl]-1-methyl-4-(1-methylethyl)-1H-[1,3,5]triazepino[3,2-a]benzimidazol-5(2H)-one
c. 1-butyl-3,4-dihydro-2-[2-(dimethylamino)ethyl]-4-(2-methylpropyl)-1H-[1,3,5]triazepino[3,2-a]benzimidazol-5(2H)-one.

EXAMPLE 12

Following the procedures of Example 3, there are obtained from N-methylpiperazine and
a. 2-(2-chloroethyl)-1-cyclohexyl-3,4-dihydro-4-methyl-1H-[1,3,5]triazepino[3,2-a]benzimidazol-5(2H)-one
b. 2-(2-chloroethyl)-1,4-diethyl-3,4-dihydro-1H-[1,3,5]triazepino[3,2-a]benzimidazol-5(2H)-one
c. 4-butyl-2-(2-chloroethyl)-3,4-dihydro-1-ethyl-1H-[1,3,5]triazepino-[3,2-a]benzimidazol-5(2H)-one
the following compounds respectively:
a. 1-cyclohexy-3,4-dihydro-4-methyl-2-[2-(4-methyl-1-piperazinyl)ethyl]-1H-[1,3,5]triazepino[3,2-a]benzimidazol-5(2H)-one
b. 3,4-dihydro-1,4-diethyl-2-[2-(4-methyl-1-piperazinyl)ethyl]-1H-[1,3,5]triazepino[3,2-a]benzimidazol-5(2H)-one
c. 4-butyl-3,4-dihydro-1-ethyl-2-[2-(4-methyl-1-piperazinyl)ethyl]-1H-[1,3,5]triazepino[3,2-a]benzimidazol-5(2H)-one.

EXAMPLE 13

Following the procedures of Example 4, there are obtained from N-methylaniline and
a. 2-(2-chloroethyl)-3,4-dihydro-1-methyl-4-(1-methylethyl)-[1,3,5]triazepino[3,2-a]benzimidazol-5(2H)-one
b. 1-butyl-2-(2-chloroethyl)-4-cyclohexyl-3,4-dihydro-1H-[1,3,5]triazepino[3,2-a]benzimidazol-5(2H)-one
c. 1-butyl-2-(2-chloroethyl)-3,4-dihydro-4-methyl-1H-[1,3,5]triazepino[3,2-a]benzimidazol-5(2H)-one
the following compounds respectively:
a. 3,4-dihydro-1-methyl-4-(1-methylethyl)-2-[2-(methylphenylamino)ethyl]-1H-[1,3,5]triazepino[3,2-a]benzimidazol-5(2H)-one
b. 1-butyl-4-cyclohexyl-3,4-dihydro-2-[2-(methylphenylamino)ethyl]-1H-[1,3,5]triazepino[3,2-a]benzimidazol-5(2H)-one
c. 1-butyl-3,4-dihydro-4-methyl-2[2-(methylphenylamino)ethyl]-1H-[1,3,5]triazepino[3,2-a]benzimidazol-5(2H)-one.

EXAMPLE 14

Following the procedure of Example 6 there are obtained from N-phenylpiperazine and
a. 2-(2-chloroethyl)-3,4-dihydro-4-hexyl-1-methyl-1H-[1,3,5]triazepino[3,2-a]benzimdazol-5(2H)-one b. 2-(2-chloroethyl)-4-cyclopentyl-3,4-dihydro-1-methyl-1H-[1,3,5]triazepino[3,2-a]benzimidazol-5(2H)-one the following compounds respectively:
a. 3,4-dihydro-4-hexyl-1-methyl-2-[2-(4-phenyl-1-piperazinyl)ethyl]-1H-[1,3,5]triazepino[3,2-a]benzimidazol-5(2H)-one
b. 4-cyclopentyl-3,4-dihydro-1-methyl-2-[2-(4-phenyl-1-piperidinyl)ethyl]-1H-[1,3,5]triazepino[3,2-a]benzimidazol-5(2H)-one.

EXAMPLE 15

Following the procedure of Example 1 and substituting for morpholine:
a. N-methylpropylamine
b. N-ethylbutylanine
c. N-methylethylamine there are obtained respectively:
a. 3,4-dihydro-1,4-dimethyl-2-[2-(N-methylpropylamino)ethyl]-1H-[1,3,5]triazepino[3,2-a]benzimidazol-5(2H)-one
b. 3,4-dihydro-1,4-dimethyl-2-[2-(N-ethylbutylamino)ethyl]-1H-[1,3,5]triazepino[3,2-a]benzimidazol-5(2H)-one
c. 3,4-dihydro-1,4-dimethyl-2-[2-(N-methylethylamino)ethyl-1H-[1,3,5]triazepino[3,2-a]benzimidazol-5(2H)-one.

PHARMACOLOGY

Muscle Relaxant Test

The test procedure relied on to indicate positive muscle relaxant activity is the morphine-induced Straub Tail in Mice Test described by G. D. Novak in DRUG DEVELOPMENT RESEARCH (1982) 2: 383-386, except 8 animals per group were used per test rather than 10. The test is summarized as follows: The test drug, reference drug, and control articles to be administered are prepared in saline, 0.5% aqueous methylcellulose suspension or other, depending on solubility, in such concentration that the volume administered is 10 ml/kg. The initial screening dose of the test drug is usually 100 mg/kg. Groups of 8 mice are given an IP dose of a compound or vehicle prepared as described above. After 15 min, mice are administered morphine sulfate, 60 mg/kg, subcutaneously. Fifteen minutes after administration of morphine (i.e., 30 min after test compound administration), mice were scored for presence of Straub Tail defined as an elevation of the tail at least 90 degrees from the horizontal. An $ED_{50}$ value may be determined from at least three logarithmically spaced doses by the method of Litchfield and Wilcoxon (1949), J. PHARMACOL. EXP. THER. 96: 99-113.

Illustratively, the compound of Example 6 exhibited an $ED_{50}$ of 4.3 mg/kg (IP) and the compound of Example 7 had an $ED_{50}$ of 15.7 mg/kg (IP).

Pharmaceutical Compositions and Administration

Compositions for administration to living warm-blooded animals are comprised of at least one of the compounds of Formula I according to the methods of treatment of the invention in association with a pharmaceutical carrier or excipient. Effective quantities of the compounds may be administered in any one of various ways, for example, orally as in elixirs, capsules, tablets or coated tablets, parenterally in the form of sterile solutions suspensions and in some cases intravenously in the form of sterile solutions, intranasally and to the throat or bronchial region in the form of drops, gargles, syrups, powders, etc. or subcutaneously. Suitable tableting excipients include lactose, potato and maize starches, talc, gelatin, stearic, and silicic acids, magnesium stearate and polyvinyl pyrrolidone.

For the parenteral administration, the carrier or excipient can be comprised of a sterile parenterally acceptable liquid, e.g., water or arachis oil contained in ampoules.

Advantageously, the compositions are formulated as dosage units, each unit being adapted to supply a fixed dose of active ingredients. Tablets, coated tablets, capsules, ampoules, sprays and suppositories are examples of preferred dosage forms. It is only necessary that the active ingredient constitute an effective amount such that a suitable effective dosage will be consistent with the dosage form employed, in multiples if necessary.

TABLE 1

| Example | R | $R^1$ | $NR^2R^3$ |
|---|---|---|---|
| 1 | $CH_3$ | $CH_3$ | 4-morpholinyl |
| 2 | $CH_3$ | $CH_3$ | $N(CH_3)_2$ |
| 3 | $CH_3$ | $CH_3$ | 4-methyl-1-piperazinyl |
| 4 | $CH_3$ | $CH_3$ | methylphenylamino |
| 5 | $CH_3$ | $CH_3$ | 4-[bis(4-fluorophenyl)methyl]-1-piperidinyl |
| 6 | $CH_3$ | $CH_3$ | 4-phenyl-1-piperazinyl |
| 7 | $CH_3$ | $CH_3$ | 4-hydroxy-4-phenyl-1-piperidinyl |
| 8 | $CH_3$ | $CH_3$ | 4-(2-pyridinyl)-1-piperazinyl |
| 9 | $CH_3$ | $CH_3$ | 4-(2-pyrimidinyl)-1-piperazinyl |
| 10a | cyclohexyl | cyclohexyl | 4-morpholinyl |
| 10b | t-butyl | t-butyl | 4-morpholinyl |
| 10c | methyl | ethyl | 4-morpholinyl |
| 11a | methyl | propyl | $-N(CH_3)_2$ |
| 11b | isopropyl | methyl | $-N(CH_3)_2$ |
| 11c | isobutyl | butyl | $-N(CH_3)_2$ |
| 12a | methyl | cyclohexyl | 4-methyl-1-piperazinyl |
| 12b | ethyl | ethyl | 4-methyl-1-piperazinyl |
| 12c | butyl | ethyl | 4-methyl-1-piperazinyl |
| 13a | isobutyl | methyl | methylphenylamino |
| 13b | cyclohexyl | butyl | methylphenylamino |
| 13c | methyl | butyl | methylphenylamino |
| 14a | n-hexyl | methyl | 4-phenyl-1-piperazinyl |
| 14b | cyclopentyl | methyl | 4-phenyl-1-piperazinyl |
| 15a | methyl | methyl | N(methyl)(propyl) |
| 15b | methyl | methyl | N(ethyl)(butyl) |
| 15c | methyl | methyl | N(methyl)(ethyl) |

The exact individual dosages, as well as daily dosages, will of course be determined according to standard medical principles under the direction of a physician or veterinarian. Generally, the following guide to projected human oral dosages is derived by knowledge of the activity obtained in the animal screening test for the muscle relaxation in the methods of the invention compared to activity of known agents in the field in the same animal screening tests. However, the amount of the active compounds administered need not be limited by these comparisons due to uncertainty in transposing comparative animal data to human treatments.

In comparison to diazepam with an $ED_{50}=1$ in the Straub Tail Test, the contemplated dosage of a compound of this invention for treating muscle tension and spasticity in an adult human is 20–200 mg daily, divided into unit doses of 8–40 mg to be taken 3 or 4 times each day.

Other routes of administration such as intravenous or intraperitoneal are possible with dosage forms being adapted to the situation as will be obvious to one skilled in the art of medicine.

Various modifications and equivalents will be apparent to one skilled in the art and may be made in the compounds, methods of treatment and compositions of the present invention without departing from the spirit or scope thereof, and it is therefore to be understood that the invention is limited only by the scope of the claims.

What is claimed:

1. (Amended) A compound having the formula:

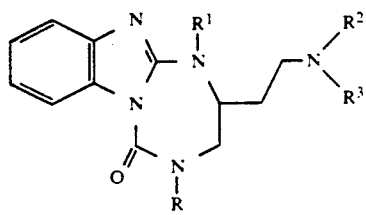

wherein:
R and $R^1$ are independently selected from $C_1$-$C_6$ alkyl or cyclopentyl or cyclohexyl; and
$R^2$ and $R^3$ are independently selected from $C_1$-$C_6$ alkyl, phenyl or phenyl substituted by 1 to 3 substituents selected from the group consisting of hydroxy, halogen, $C_1$-$C_4$ alkoxy, trifluoromethyl, nitro or amino or $R^2$ and $R^3$ taken together with the interposing nitrogen atom forms a saturated heterocyclic group selected from morpholine, piperidine, 4-[bis(4-fluorophenyl)methyl]piperidine, 4-hydroxy-4-phenylpiperidine, piperazine, 4-($C_1$-$C_6$ alkyl)piperazine, 4-phenylpiperazine, 4-(2-pyridinyl)piperazine, or 4-(2-pyrimidinyl)piperazine; the optical isomers and the pharmaceutically acceptable salts thereof.

2. A compound according to claim 1 wherein R and $R^1$ are methyl.

3. A compound according to claim 2 which is 3,4-dihydro-1,4-dimethyl-2-[2-(4-morpholinyl)ethyl]-1H-[1,3,5]triazepino[3,2-a]benzimidazol-5-(2H)-one, the optical isomers or a pharmaceutically acceptable salt thereof.

4. A compound according to claim 2 which is 2-[2-(dimethylamino)ethyl]-3,4-dihydro-1,4-dimethyl-1H-[1,3,5]triazepino[3,2-a]benzimidazol-5-(2H)-one, the optical isomers, or a pharmaceutically acceptable salt thereof.

5. A compound according to claim 2 which is 3,4-dihydro-1,4-dimethyl-2-[2-(4-methyl-1-piperazinyl)ethyl]-1H-[1,3,5]triazepino[3,2-a]benzimidazol-5(2H)-one, the optical isomers or a pharmaceutically acceptable salt thereof.

6. A compound according to claim 2 which is 3,4-dihydro-1,4-dimethyl-2-[2-(4-phenyl-1-piperazinyl)ethyl]-1H-[1,3,5]triazepino[3,2-a]benzimidazol-5(2H)-one, the optical isomers or a pharmaceutically acceptable salt thereof.

7. A compound according to claim 2 which is 3,4-dihydro-2-[2-(4-hydroxy-4-phenyl-1-piperidinyl)ethyl]-1,4-dimethyl-1H-[1,3,5]triazepino[3,2-a]benzimidazol-5(2H)-one, the optical isomers or a pharmaceutically acceptable salt thereof.

8. A compound according to claim 2 which is 3,4-dihydro-1,4-dimethyl-2-[2-[4-(2-pyridinyl)-1-piperazinyl]ethyl]-1H-[1,3,5]triazepino[3,2-a]benzimidazol-5(2H)-one, the optical isomers or a pharmaceutically acceptable salt thereof.

9. A compound according to claim 2 which is 3,4-dihydro-1,4-dimethyl-2-[2-[4-(2-pyrimidinyl)-1-piperazinyl]ethyl]-1H-[1,3,5]triazepino[3,2-a]benzimidazol-5(2H)-one, the optical isomers or a pharmaceutically acceptable salt thereof.

10. A compound according to claim 2 which is 3,4-dihydro-1,4-dimethyl-2-[2-(methylphenylamino)ethyl]-1H-[1,3,5]triazepino[3,2-a]benzimidazol-5(2H)-one, the optical isomers or a pharmaceutically acceptable salt thereof.

11. A compound according to claim 2 which is 2-[2-[4-[bis(4-fluorophenyl)-methyl]-1-piperidinyl]ethyl]-3,4-dihydro-1,4-dimethyl-1H-[1,3,5]triazepino[3,2-a]benzimidazol-5(2H)-one, the optical isomers or a pharmaceutically acceptable salt thereof.

12. (Amended) A method of treating muscle tension and spasticity in warm-blooded animals by administering thereto a therapeutically effective amount of a compound having the formula:

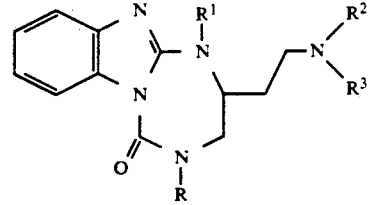

wherein:
R and $R^1$ are independently selected from $C_1$-$C_6$ alkyl or cyclopentyl or cyclohexyl; and
$R^2$ and $R^3$ are independently selected from $C_1$-$C_6$ alkyl, phenyl or phenyl substituted by 1 to 3 substituents selected from the group consisting of hydroxy, halogen, $C_1$-$C_4$ alkoxy, trifluoromethyl, nitro or amino or $R^2$ and $R^3$ taken together with the interposing nitrogen atom forms a saturated heterocyclic group selected from morpholine, piperidine, 4-[bis(4-fluorophenyl)methyl]piperidine, 4-hydroxy-4-phenylpiperidine, piperazine, 4-($C_1$-$C_6$ alkyl)piperazine, 4-phenylpiperazine, 4-(2-pyridinyl)piperazine, or 4-(2-pyrimidinyl)piperazine; the optical isomers and the pharmaceutically acceptable salts thereof.

13. A method according to claim 12 where the therapeutically effective compound used is selected from:
3,4-dihydro-1,4-dimethyl-2-[2-(4-morpholinyl)ethyl]-1H-[1,3,5]triazepino[3,2-a]benzimidazol-5(2H)-one,
2-[2-(dimethylamino)ethyl]-3,4-dihydro-1,4-dimethyl-1H-[1,3,5]triazepino[3,2-a]benzimidazol-5(2H)-one,
3,4-dihydro-1,4-dimethyl-2-[2-(4-methyl-1-piperazinyl)ethyl]-1H-[1,3,5]triazepino[3,2-a]benzimidazol-5(2H)-one,
3,4-dihydro-1,4-dimethyl-2-[2-(methylphenylamino)ethyl]-1H-[1,3,5]triazepino[3,2-a]benzimidazol-5(2H)-one,
2-[2-[4-[bis(4-fluorophenyl)methyl]-1-piperidinyl]ethyl]-3,4-dihydro-1,4-dimethyl-1H-[1,3,5]triazepino[3,2-a]benzimidazol-5(2H)-one,
3,4-dihydro-1,4-dimethyl-2-[2-(4-phenyl-1-piperazinyl)ethyl]-1H-[1,3,5]triazepino[3,2-a]benzimidazol-5(2H)-one,
3,4-dihydro-2-[2-(4-hydroxy-4-phenyl-1-piperidinyl)ethyl]-1,4-dimethyl-1H-[1,3,5]triazepino[3,2-a]benzimidazol-5(2H)-one,
3,4-dihydro-1,4-dimethyl-2-[2-[4-(2-pyridinyl)-1-piperazinyl]ethyl]-1H-[1,3,5]triazepino[3,2-a]benzimidazol-5(2H)-one.
3,4-dihydro-1,4-dimethyl-2-[2-[4-(2-pyrimidinyl)-1-piperazinyl]ethyl]-1H-[1,3,5]triazepino[3,2-a]benzimidazol-5(2H)-one,
the optical isomers or a pharmaceutically acceptable salt thereof.

14. A pharmaceutical composition for the treatment of muscle tension and spasticity comprising:
a. a therapeutically effective amount of a compound having the formula:

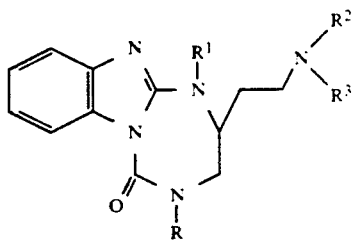

wherein:

R and $R^1$ are independently selected from $C_1$-$C_6$ alkyl or cyclopentyl or cyclohexyl; and
$R^2$ and $R^3$ are independently selected from $C_1$-$C_6$ alkyl, phenyl or phenyl substituted by 1 to 3 substituents selected from the group consisting of hydroxy, halogen, $C_1$-$C_4$ alkoxy, trifluoromethyl, nitro and amino or $R^2$ and $R^3$ taken together with the interposing nitrogen forms a saturated heterocyclic group selected from morpholine, piperidine, 4-[bis(4-fluorophenyl)methyl]piperidine, 4-hydroxy-4-phenylpiperazine, piperazine, 4-($C_1$-$C_6$ alkyl)piperazine, 4-phenylpiperazine, 4-(2-pyridinyl)piperazine and 4-(2-pyrimidinyl)piperazine; the optical isomers or a pharmaceutically acceptable salt thereof; and
b. a pharmaceutical carrier.

15. A pharmaceutical composition according to claim 14 wherein the therapeutically effective compound used is selected from:
3,4-dihydro-1,4-dimethyl-2-[2-(4-morpholinyl)ethyl]-1H-[1,3,5]triazepino[3,2-a]benzimidazol-5(2H)-one,
2-[2-(dimethylamino)ethyl]-3,4-dihydro-1,4-dimethyl-1H-[1,3,5]triazepino[3,2-a]benzimidazol-5(2H)-one,
3,4-dihydro-1,4-dimethyl-2-[2-(4-methyl-1-piperazinyl)ethyl]-1H-[1,3,5]triazepino[3,2-a]benzimidazol-5(2H)-one,
3,4-dihydro-1,4-dimethyl-2-[2-(methylphenylamino)ethyl]-1H-[1,3,5]triazepino[3,2-a]benzimidazol-5(2H)-one,
2-[2-[4-[bis(4-fluorophenyl)methyl]-1-piperidinyl]ethyl]-3,4-dihydro-1,4-dimethyl-1H-[1,3,5]triazepino[3,2-a]benzimidazol-5(2H)-one,
3,4-dihydro-1,4-dimethyl-2-[2-(4-phenyl-1-piperazinyl)ethyl]-1H-]1,3,5]triazepino[3,2-a]benzimidazol-5(2H)-one,
3,4-dihydro-2-[2-(4-hydroxy-4-phenyl-1-piperidinyl)ethyl]-1,4-dimethyl-1H-[1,3,5]triazepino[3,2-a]benzimidazol-5(2H)-one,
3,4-dihydro-1,4-dimethyl-2-[2-[4-(2-pyridinyl)-1-piperazinyl]ethyl]-1H-[1,3,5]triazepino[3,2-a]benzimidazol-5(2H)-one,
3,4-dihydro-1,4-dimethyl-2-[2-[4-(2-pyrimidinyl)-1-piperazinyl]ethyl]-1H-[1,3,5]triazepino[3,2-a]benzimidazol-5(2H)-one,
the optical isomers, or a pharmaceutically acceptable salt thereof.

* * * * *